US00PP26006P2

(12) United States Plant Patent
Graff

(10) Patent No.: US PP26,006 P2
(45) Date of Patent: Oct. 20, 2015

(54) ***HIBISCUS* PLANT NAMED 'ADONIS YELLOW'**

(50) Latin Name: *Hibiscus rosa-sinensis*
Varietal Denomination: Adonis Yellow

(71) Applicant: Poul Graff, Sabro (DK)

(72) Inventor: Poul Graff, Sabro (DK)

(73) Assignee: Graff Breeding A/S, Sabro (DK)

( * ) Notice: Subject to any disclaimer, the term of this patent is extended or adjusted under 35 U.S.C. 154(b) by 46 days.

(21) Appl. No.: 13/999,138

(22) Filed: Jan. 21, 2014

(51) Int. Cl.
*A01H 5/02* (2006.01)

(52) U.S. Cl.
USPC ..... Plt./257

(58) Field of Classification Search
USPC ..... Plt./257
CPC ..... A01H 5/02; A01H 5/00
See application file for complete search history.

*Primary Examiner* — Kent L Bell
(74) *Attorney, Agent, or Firm* — C. A. Whealy

(57) ABSTRACT

A new and distinct cultivar of *Hibiscus* plant named 'Adonis Yellow', characterized by its upright, mounding and bushy plant habit; dark green-colored leaves; uniform and freely flowering habit; large yellow-colored flowers with dark red-colored centers; and excellent flower longevity.

4 Drawing Sheets

Botanical designation: *Hibiscus rosa-sinensis*.
Cultivar denomination: 'ADONIS YELLOW'.

BACKGROUND OF THE INVENTION

The present invention relates to a new and distinct cultivar of *Hibiscus* plant, botanically known as *Hibiscus rosa-sinensis*, and hereinafter referred to by the name 'Adonis Yellow'.

The new *Hibiscus* plant is a product of a planned breeding program conducted by the Inventor in Sabro, Denmark. The objective of the breeding program is to create new strong *Hibiscus* plants with attractive and long-lasting flowers.

The new *Hibiscus* plant is a naturally-occurring branch mutation of *Hibiscus rosa-sinensis* 'Adonis', disclosed in U.S. Plant Pat. No. 21,592. The new *Hibiscus* plant was discovered and selected by the Inventor on a single flowering plant within a population of plants of 'Adonis' in a controlled greenhouse environment in Sabro, Denmark in May, 2011.

Asexual reproduction of the new *Hibiscus* plant by vegetative terminal cuttings in a controlled greenhouse environment in Sabro, Denmark since September, 2011 has shown that the unique features of this new *Hibiscus* plant are stable and reproduced true to type in successive generations.

SUMMARY OF THE INVENTION

Plants of the new *Hibiscus* have not been observed under all possible combinations of environmental conditions and cultural practices. The phenotype may vary somewhat with variations in environmental conditions such as temperature and light intensity without, however, any variance in genotype.

The following traits have been repeatedly observed and are determined to be the unique characteristics of 'Adonis Yellow'. These characteristics in combination distinguish 'Adonis Yellow' as a new and distinct *Hibiscus* plant:

1. Upright, mounding and bushy plant habit.
2. Dark green-colored leaves.
3. Uniform and freely flowering habit.

4. Large yellow-colored flowers with dark red-colored centers.
5. Excellent flower longevity.

Plants of the new *Hibiscus* can be compared to plants of the parent, 'Adonis'. Plants of the new *Hibiscus* differ primarily from plants of 'Adonis' in flower bud and petal color as of plants of 'Adonis' have red purple-colored flower buds and petals.

Plants of the new *Hibiscus* can be compared to plants of the *Hibiscus rosa-sinensis* 'Boreas Yellow', disclosed in U.S. Plant Pat. No. 24,060. In side-by-side comparisons conducted in Sabro, Denmark, plants of the new *Hibiscus* differed from plants of 'Boreas Yellow' in the following characteristics:

1. Leaves of plants of the new *Hibiscus* were more ovate to cordate in shape and darker in color than leaves of plants of 'Boreas Yellow'.
2. Plants of the new *Hibiscus* and 'Boreas Yellow' differed in stigma color.
3. Flowers of plants of the new *Hibiscus* lasted about three to four days whereas flowers of plants of 'Boreas Yellow' lasted four to five days.

BRIEF DESCRIPTION OF THE PHOTOGRAPHS

The accompanying colored photographs illustrate the overall appearance of the new *Hibiscus* plant showing the colors as true as it is reasonably possible to obtain in colored reproductions of this type. Colors in the photographs may differ slightly from the color values cited in the detailed botanical description which accurately describe the colors of the new *Hibiscus* plant.

The photograph on the first sheet comprises a side perspective view of a typical flowering plant of 'Adonis Yellow' grown in a container.

The photograph on the second sheet is a close-up view of the upper and lower surfaces of typical leaves of 'Adonis Yellow'.

The photograph on the third sheet is a close-up view of typical developing flower buds and a typical open flower of 'Adonis Yellow'.

The photograph on the fourth sheet is a close-up view of a typical dissected flower of 'Adonis Yellow'.

DETAILED BOTANICAL DESCRIPTION

The aforementioned photographs and following observations, measurements and values describe plants grown during the autumn and winter in 13-cm containers in a glass-covered greenhouse in Sabro, Denmark and under environmental conditions and cultural practices which closely approximate commercial *Hibiscus* production. During the production of the plants, day temperatures ranged from 20° C. to 25° C., night temperatures ranged from 19° C. to 21° C. and light levels ranged from 40 to 50 klux. Plants were pinched one time about eight to nine weeks after planting and plants were 21 weeks old when the photographs and the description were taken. In the description, color references are made to The Royal Horticultural Society Colour Chart, 2001 Edition, except where general terms of ordinary dictionary significance are used.

Botanical classification: *Hibiscus rosa-sinensis* 'Adonis Yellow'.

Parentage: Naturally-occurring branch mutation of *Hibiscus rosa-sinensis* 'Adonis', disclosed in U.S. Plant Pat. No. 21,592.

Propagation:

*Type*.—By vegetative terminal cuttings.

*Time to initiate roots, summer*.—About three weeks at temperatures about 24° C.

*Time to initiate roots, winter*.—About four weeks at temperatures about 24° C.

*Time to produce a rooted young plant, summer*.—About eight weeks at temperatures about 24° C.

*Time to produce a rooted young plant, winter*.—About nine weeks at temperatures about 24° C.

*Root description*.—Medium in thickness, fleshy; color, close to 158A.

*Rooting habit*.—Freely branching; dense.

Plant description:

*Plant and growth habit*.—Upright, mounding and bushy plant habit; moderately vigorous growth habit.

*Branching habit*.—Freely branching habit with usually about four to six lateral branches developing per plant; pinching enhances lateral branch development.

*Plant height*.—About 35 cm to 55 cm.

*Plant diameter* (*area of spread*).—About 30 cm to 50 cm.

Lateral branch description:

*Length*.—About 15 cm to 25 cm.

*Diameter*.—About 3 mm to 6 mm.

*Internode length*.—About 1 cm to 5 cm.

*Strength*.—Strong.

*Texture*.—Woody.

*Color*.—Close to N199A.

Leaf description:

*Arrangement*.—Alternate, single; numerous.

*Length*.—About 8 cm to 12 cm.

*Width*.—About 5 cm to 8 cm.

*Shape*.—Ovate to cordate.

*Apex*.—Acuminate.

*Base*.—Cordate.

*Margin*.—Crenate.

*Texture, upper surface*.—Smooth, glabrous; venation slightly prominent.

*Texture, lower surface*.—Scattered pubescence; venation prominent.

*Luster, upper and lower surfaces*.—Slightly glossy.

*Venation pattern*.—Pinnate; arcuate.

*Color*.—Developing leaves, upper surface: Close to 139A. Developing leaves, lower surface: Close to 146A. Fully expanded leaves, upper surface: Close to N189A; venation, close to 147B. Fully expanded leaves, lower surface: Close to 137A; venation, close to 147B.

*Petioles*.—Length: About 3 cm to 5 cm. Diameter: About 2 mm. Texture, upper and lower surfaces: Pubescent. Color, upper surface: Close to 147A and N199B. Color, lower surface: Close to 146A and N199B.

Flower description:

*Flower arrangement*.—Flowers arranged singly at terminal leaf axils; uniform, continuous and freely flowering habit with numerous flower buds and open flowers per plant at one time; flowers face mostly upright to slightly outwardly.

*Fragrance*.—None detected.

*Natural flowering season*.—Plants flower in the garden during the spring and summer or during periods of warm weather; in the greenhouse, plants can be flowered year-round; plants begin flowering about ten to twelve weeks after pinching.

*Flower longevity*.—Excellent flower longevity, flowers last for about three to four days; flowers persistent.

*Flower diameter*.—About 16 cm to 19 cm.

*Flower length* (*height*).—About 8 cm to 9 cm.

*Flower buds*.—Rate of opening: Flowers buds open in about two to three days. Length: About 7 cm to 8 cm. Diameter: About 2.5 cm to 3.5 cm. Shape: Ovate to lanceolate. Color: Close to 10A.

*Petals*.—Arrangement: Five imbricate petals in a single whorl. Length: About 8 cm to 10 cm. Width: About 8 cm to 9 cm. Shape: Fan-shaped. Apex: Rounded. Base: Attenuate. Margin: Entire, slightly undulate. Texture, upper surface: Glabrous, rugose; slightly prominent venation. Texture, lower surface: Glabrous, rugose; prominent venation. Luster, upper and lower surfaces: Matte. Color: When opening, upper surface: Close to 8B; towards the base, close to 46B. When opening, lower surface: Close to 9D. Fully opened, upper surface: Close to 12A to 12B; towards the base, close to 53A; with development, colors becoming closer to 14B and closer to 59A towards the base. Fully opened, lower surface: Close to 11A; with development, color becoming closer to 14C.

*Sepals*.—Appearance: Five sepals fused into a campanulate-shaped calyx. Length: About 3 cm to 3.5 cm. Width: About 1 cm to 1.5 cm. Shape: Lanceolate. Apex: Acuminate. Margin: Entire. Texture, upper surface: Rugose, pubescent; prominent venation. Texture, lower surface: Pubescent; recessed venation. Color, upper surface: Close to 143B. Color, lower surface: Close to 144A.

*Peduncles*.—Length: About 2.5 cm to 3.5 cm. Diameter: About 3 mm to 4 mm. Strength: Strong. Texture: Sparsely pubescent. Color: Close to 146A.

*Reproductive organs*.—Androecium: Stamen number: Numerous, about 100. Filament length: About 2 mm to 3 mm. Filament color: Close to 11D. Anther shape: Ovate. Anther length: About 1 mm to 2 mm. Anther color: Close to 19A. Amount of pollen: Abundant. Pollen color: Close to 17B. Gynoecium: Pistil length: About 8 cm to 10 cm. Style length: About 7 cm to 9 cm. Style texture: Smooth, waxy. Style color: Close to 2D. Stigma appearance: Five-parted, rounded. Stigma color: Close to 16D. Ovary color: Close to 145A.

*Seeds*.—Quantity produced per flower: About 1 to 20. Length: About 4 mm to 5 mm. Diameter: About 3 mm to 4 mm. Color: Close to 202A.

Temperature tolerance: Plants of the new *Hibiscus* have been observed to have tolerate temperatures from about 1° C. to about 30° C.

Pathogen & pest resistance: Plants of the new *Hibiscus* have not been observed to be resistant to pathogens and pests common to *Hibiscus* plants.

It is claimed:

1. A new and distinct *Hibiscus* plant named 'Adonis Yellow' as illustrated and described.

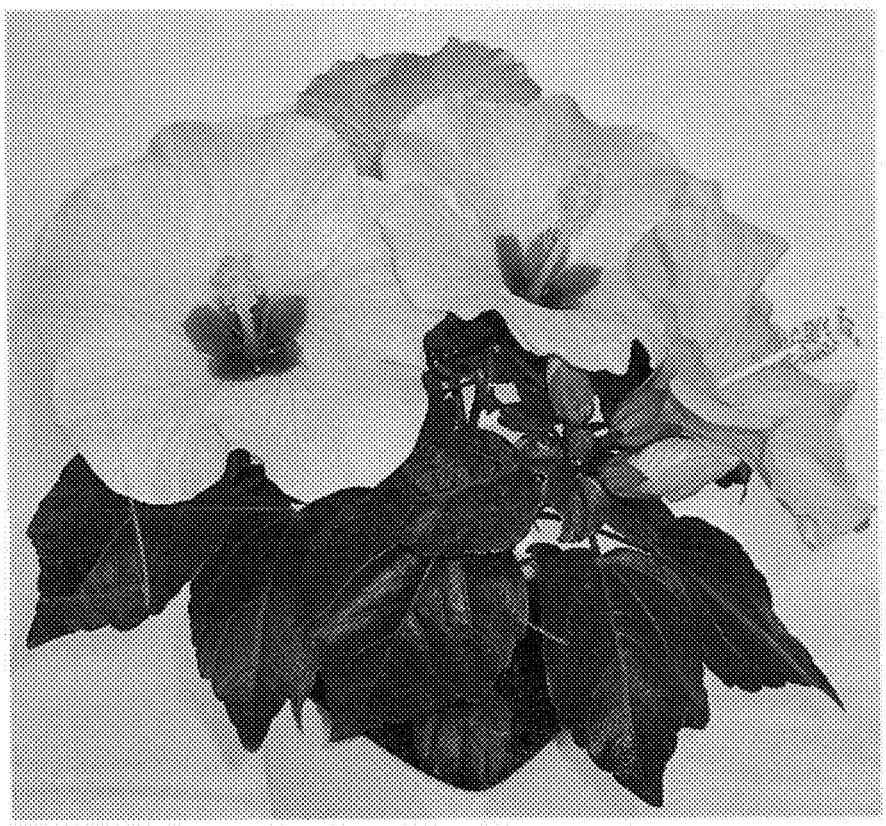

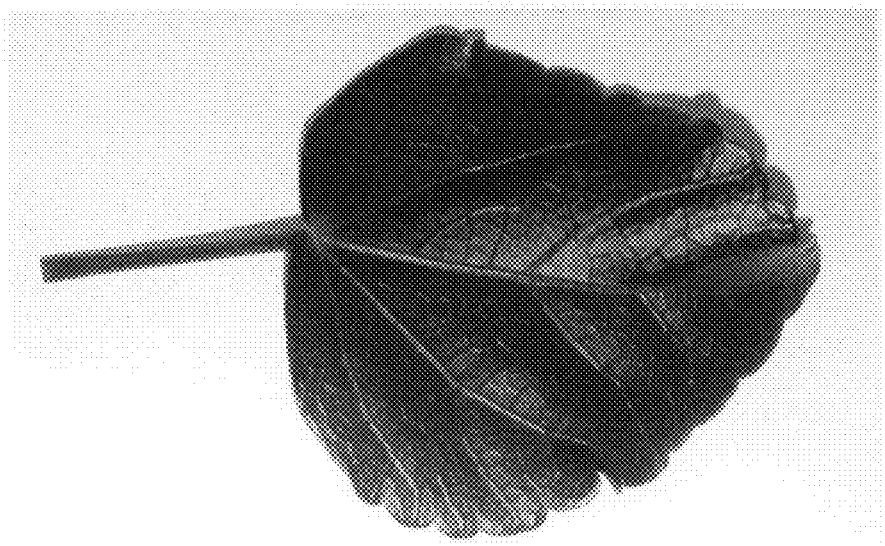
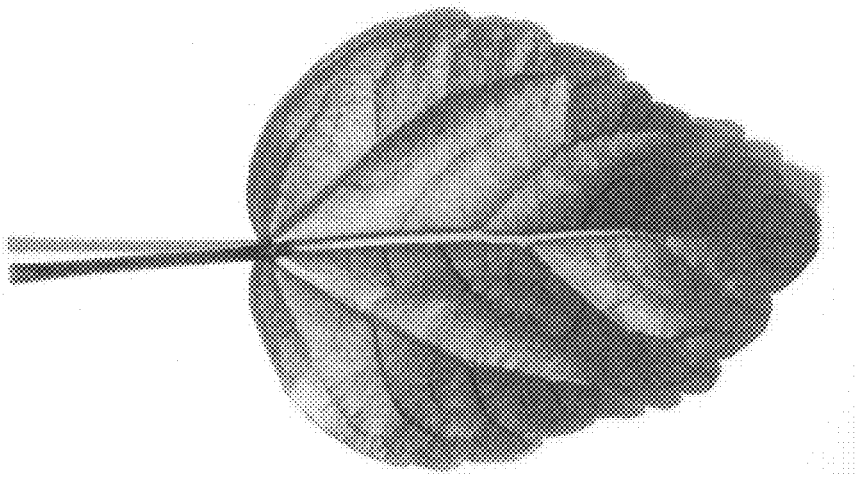

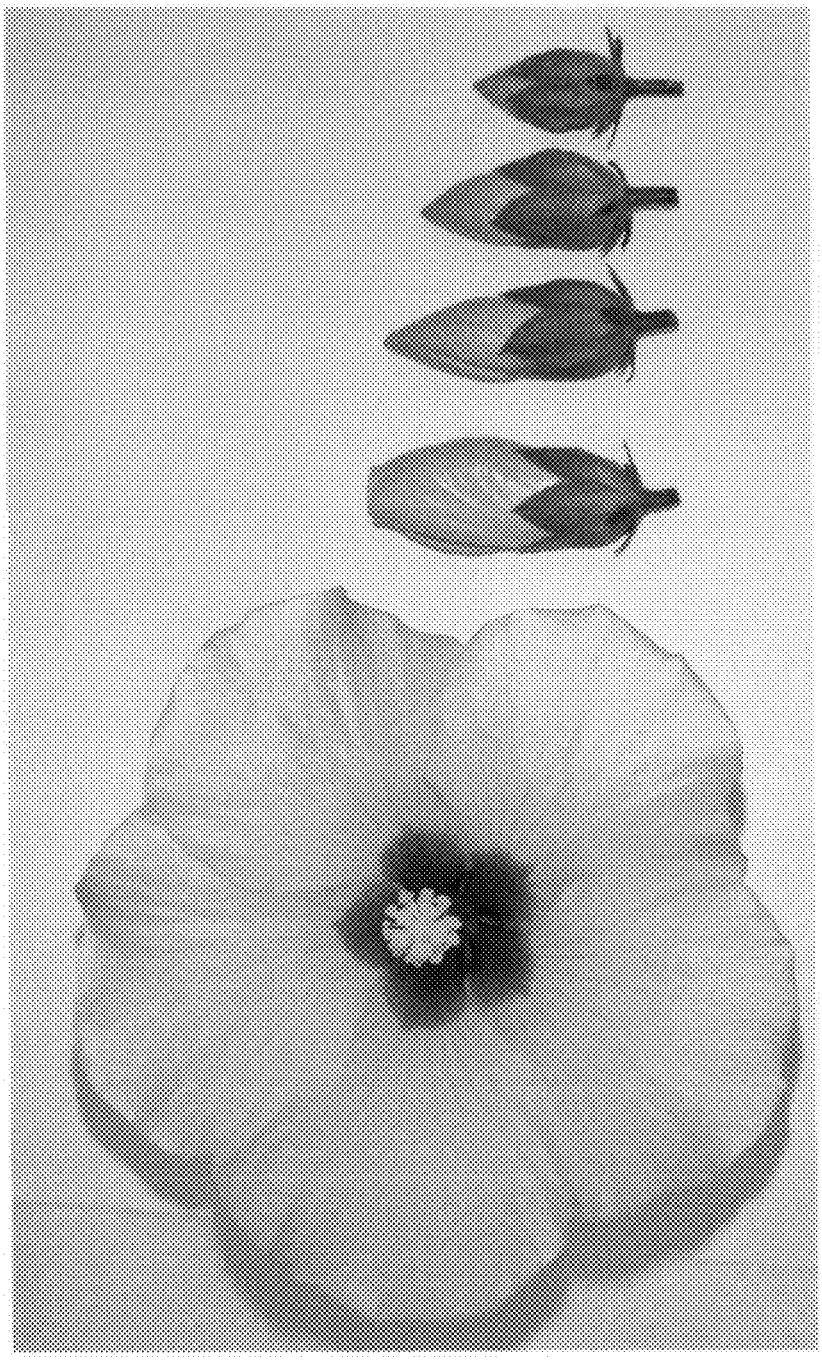

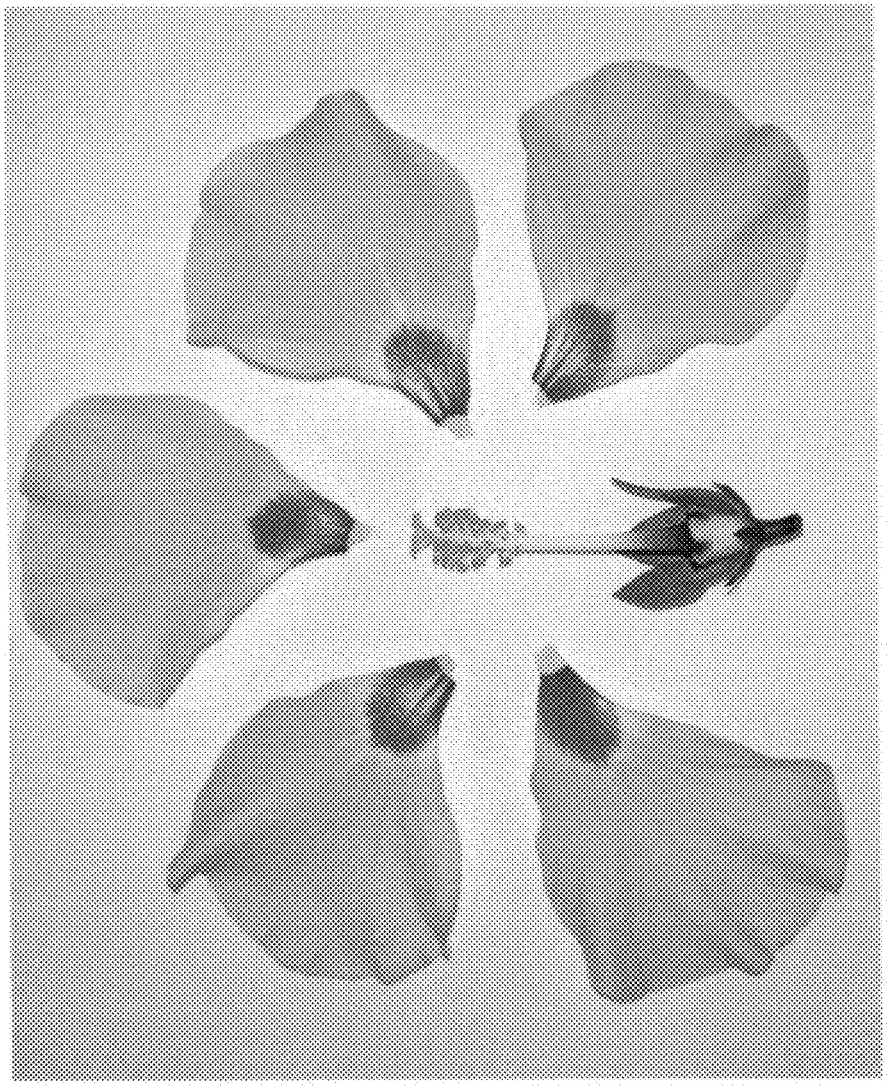

* * * * *